US008397723B2

(12) United States Patent
Conrad et al.

(10) Patent No.: US 8,397,723 B2
(45) Date of Patent: Mar. 19, 2013

(54) EMERGENCY OXYGEN SUPPLY DEVICE

(75) Inventors: Rüdiger Conrad, Stockelsdorf (DE); Heiko Marz, Lübeck (DE); Kristina Kurz, Bad Schwartau (DE)

(73) Assignee: B/E Aerospace Systems GmbH, Lübeck (DE)

( * ) Notice: Subject to any disclaimer, the term of this patent is extended or adjusted under 35 U.S.C. 154(b) by 301 days.

(21) Appl. No.: 12/850,807

(22) Filed: Aug. 5, 2010

(65) Prior Publication Data

US 2011/0036351 A1 Feb. 17, 2011

(30) Foreign Application Priority Data

Aug. 13, 2009 (DE) ........................ 10 2009 037 380

(51) Int. Cl.
*A62B 7/00* (2006.01)
*A62B 9/00* (2006.01)
*A62B 9/02* (2006.01)
*A62B 18/02* (2006.01)
*A62B 31/00* (2006.01)
*A61M 16/00* (2006.01)

(52) U.S. Cl. ......... 128/205.11; 128/204.18; 128/204.21; 128/204.22; 128/204.23; 128/205.24; 128/205.25; 128/205.26; 244/118.5

(58) Field of Classification Search ........................ None
See application file for complete search history.

(56) References Cited

U.S. PATENT DOCUMENTS 5,626,131 A * 5/1997 Chua et al. ............... 128/204.23
2005/0153648 A1* 7/2005 Horner et al. .................... 454/74
2008/0053541 A1* 3/2008 Meckes et al. ........... 137/624.27
2010/0012123 A1* 1/2010 Rittner et al. ............ 128/204.21

FOREIGN PATENT DOCUMENTS

DE 32 31 172 C1 3/1984
DE 102006013538 A1 10/2007
WO WO 2007/118494 A1 10/2007

* cited by examiner

*Primary Examiner* — Melanie Hand
*Assistant Examiner* — Joshua Lee
(74) *Attorney, Agent, or Firm* — McGlew and Tuttle, P.C.

(57) ABSTRACT

An emergency oxygen supply device for an aircraft comprises an oxygen pressure tank, and at least one oxygen mask which is conductively connected thereto. At least two electrically actuatable and activatable shut-off valves which are arranged parallel to one another are arranged in the conduit from the oxygen pressure tank to the at least one oxygen mask. Of these shut-off valves, at least one shut-off valve has an NO-function and at least one shut-off valve an NC-function.

20 Claims, 1 Drawing Sheet

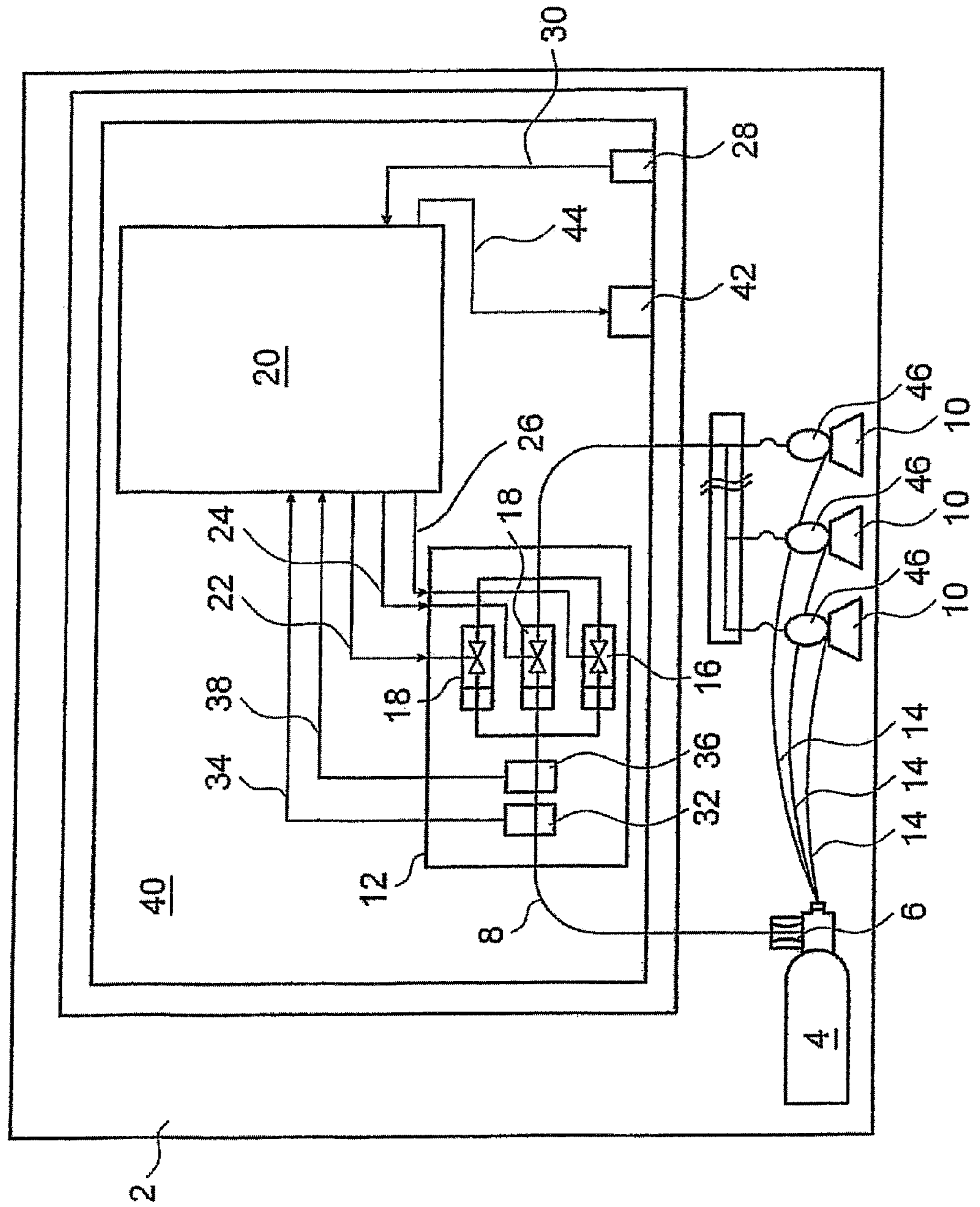
30
28
44
42
20
26
46
10
46
10
46
10
24
22
18
18
16
38
34
36
32
14
14
14
14
40
12
8
6
4
2

EMERGENCY OXYGEN SUPPLY DEVICE

CROSS REFERENCE TO RELATED APPLICATIONS

This application claims the benefit of priority under 35 U.S.C. §119 of German Patent Application DE 10 2009 037 380.2 filed Aug. 13, 2009, the entire contents of which are incorporated herein by reference.

FIELD OF THE INVENTION

The invention relates to an emergency oxygen supply device for an aircraft, with an oxygen pressure tank and with at least one oxygen mask which is conductively connected thereto.

BACKGROUND OF THE INVENTION

Emergency oxygen supply devices are available in aircraft, in order to be able to supply passengers and service personnel with oxygen in the case of a sudden pressure drop in the cabin. With a decentralized emergency oxygen supply, the emergency oxygen supply devices are located in the so-called personal service units, which are arranged on the cabin ceiling above the passenger seats.

These emergency oxygen supply devices have an oxygen source which is conductively connected to one or more oxygen masks. It is known to use chemical oxygen generators or oxygen pressure tanks as oxygen sources. Chemical oxygen generators have the disadvantage that the release of the oxygen from a chemical compound and the oxygen flow to the oxygen masks which this entails, as well as the supply pressure to the oxygen masks, follow a fixed given profile. Thus with these systems, it is not possible to control the oxygen supply in dependence on the cabin pressure or the flight altitude.

With the use of gaseous oxygen stored in compressed gas containers, the oxygen supply may be controlled in a suitable manner by way of a pressure regulation device arranged upstream of the oxygen masks. The applied pressure regulation devices may comprise pressure controllers which are actuated in a mechanical and/or pneumatic manner, whose dimensions and weight however are disadvantageously relatively large. Electrically operated regulation units do not have this disadvantage, but with these regulation units, the dependency on an electrical energy supply per se has been found to be problematic, since a failure of the electricity supply may lead to the emergency oxygen supply device not being capable of application at all.

SUMMARY OF THE INVENTION

Against this background, it is the object of the invention to provide a lightweight and compact emergency oxygen supply device for an aircraft, which ensures an adequate emergency oxygen supply in an emergency situation.

According to the invention, an emergency oxygen supply device is provided for an aircraft, with an oxygen pressure tank and with at least one oxygen mask, which is conductively connected thereto. At least two electrically actuatable and activatable shut-off valves are arranged parallel to one another in the conduit system from the oxygen pressure tank to the at least one oxygen mask. At least one shut-off valve has an NO-function (normally open function) and at least one shut-off valve has an NC-function (normally closed function).

The emergency oxygen supply device according to the invention, for an aircraft, may e.g, be arranged in a personal service unit. It comprises an oxygen pressure tank and at least one oxygen mask which is conductively connected thereto. According to the invention, at least two electrically actuatable and activatable shut-off valves which are arranged parallel to one another and are arranged in the conduit (in the conduit system) from the oxygen pressure tank to the at least one oxygen mask. Of these shut-off valves, at least one shut-off valve has a NO-function and at least one shut-off valve has a NC-function.

Thus with the emergency oxygen supply device according to the invention, a conduit branch at which the conduit divides into at least two conduit lines parallel to one another, is provided in the conduit from the oxygen pressure tank to the oxygen mask. In each case, a shut-off valve is arranged in each of these conduit lines, of which one has an NO-function or "normal open"-function, i.e, is opened with no applied voltage, whilst at least one shut-off valve is arranged in the remaining conduit lines and has an NC-function or "normal closed"-function, thus is closed with no applied voltage. With a larger number of parallel conduit lines, one may also envisage more than one shut-off valve with an NO-function and/or more than one shut-off valve with an NC-function.

The shut-off valves form part of a control device, with which the oxygen supply from the oxygen pressure tank to the oxygen mask or to the oxygen masks, may be controlled by way of a cycled opening and closure of the shut-off valves. On account of the comparatively low size and low weight of the shut-off valves compared to the mechanically or pneumatically actuated pressure regulators, which are otherwise used as closed-loop control devices, the emergency oxygen supply device according to the invention has been found to have a comparatively compact constructional shape with a low weight.

Since, with the emergency oxygen supply device according to the invention, at least one shut-off valve has an NO-function in one of the parallel conduit branches, even with a failure of the electricity supply of the emergency oxygen supply device, an at least basic supply of oxygen to the user or users of the oxygen masks is ensured, since after actuation of an opening mechanism of the oxygen pressure tank by way of a pull means connected to the oxygen mask, oxygen may flow from the oxygen pressure tank which is then opened, via the shut-off valve which is set in an open manner with no applied voltage, to the oxygen mask or masks even with an interrupted electrical power supply. This shut-off valve is preferably designed such that with a failure of the electricity supply to the emergency oxygen supply device, oxygen with a dedicated volume flow available to each user of an oxygen mask. Typically, as the case may be, it is also possible to provide several shut-off valves with an NO-function in several parallel conduit lines, wherein the number of these shut-off valves as a rule will depend on the number of persons to be provided with oxygen by the emergency oxygen supply.

Usefully, an electronic control device, with which the individual shut-off valves may be activated, is provided, so that the user of the emergency oxygen supply device according to the invention is supplied with oxygen in a manner which is matched to the respective flight altitude. The control device is advantageously designed in a manner such that the shut-off valves may be activated by it in a pulse-width modulated manner. Hereby, the duty cycle is mainly dependent on the pressure prevailing in the cabin or the flight altitude, the temperature of the oxygen and the exit pressure of the oxygen pressure tank or of a pressure controller of the oxygen pressure tank.

Usefully, the cabin pressure is continuously determined during the application of the emergency oxygen supply device. Advantageously, a cabin pressure sensor, to which the control device is signal connected, may be usefully provided for this. The shut-off valves may be activated in the required manner by way of the control device, on the basis of pressure values which are provided by the cabin pressure sensor and which are typically related to the respective flight altitude.

Preferably, an oxygen pressure sensor, which is signal connected to the control device, is arranged in the conduit connecting the oxygen pressure tank to the oxygen mask or masks, at the entry side of the shut-off valves, in order to also be able to take into account the exit pressure of the oxygen pressure tank or of the pressure controller, on activation of the shut-off valves.

Further advantageously, a temperature sensor signal-connected to the control device may be arranged in the conduit connecting the oxygen pressure tank to the oxygen mask or masks, at the entry side of the shut-off valves, in order to also include the temperature of the oxygen when determining the most useful opening intervals of the shut-off valves.

The emergency oxygen supply device according to the invention has a very high control accuracy due to the fact that, apart from the cabin pressure, advantageously the temperature of the oxygen and the oxygen pressure prevailing at the exit side of the oxygen tank or pressure reducer attached to the tank are also used for the control of the oxygen supply to the oxygen mask or to the oxygen masks. This very high control accuracy permits the saving of oxygen compared to the emergency oxygen supply devices which were known until now, which in turn renders possible the use of comparatively smaller oxygen pressure tanks and thus also reduces the size and weight of the emergency oxygen supply device, compared to devices of this type which have been known until now.

The sensors which are signal-connected to the control device are preferably arranged on a control panel of the control device. Accordingly, with this further formation of the emergency oxygen supply device according to the invention, a carrier element is provided, on which, apart from the control device, also the cabin pressure sensor, the oxygen pressure sensor and the temperature sensor, as well as preferably also the shut-off valves may be arranged.

In order to smooth the pulse-width modulated oxygen flow which is provided by the shut-off valves, into a quasi continuous oxygen flow, a compensation chamber is provided, preferably at the exit side of the shut-off valves. This compensation chamber may for example be formed by a cross-sectional widening of the oxygen conduit in the region from the shut-off valves to the oxygen mask or masks. Apart from this, an oxygen intermediate tank formed on the oxygen mask, or the oxygen conduit in the region from the shut-off valves to the oxygen mask or masks itself, may form the compensation chamber.

The invention is hereinafter explained in more detail by way of one embodiment example represented in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a greatly simplified basic view of an emergency oxygen supply device according to the invention.

DESCRIPTION OF THE PREFERRED EMBODIMENTS

Referring to the drawings in particular, the represented emergency oxygen supply device is arranged in a receptacle 2 in a personal service unit. It has an oxygen pressure tank 4 in the form of an oxygen cylinder 4. A pressure reducer 6, with which the oxygen pressure prevailing in the oxygen cylinder 4 may be reduced to a medium pressure, is provided on the oxygen cylinder 4 in the usual manner. The medium pressure lies between the bottle pressure and the required pressure at the oxygen masks 10 connected to the oxygen cylinder 4.

An oxygen conduit 8 which is connected at the exit side of the pressure reducer 6, connects the oxygen cylinder 4 to the oxygen masks 10 in an oxygen-leading manner, wherein a flow control device 12 is arranged in the conduit connection from the oxygen cylinder 4 to the oxygen masks 10, with which flow control device the oxygen quantity or oxygen flow may be finally adapted to the quantity demanded at the oxygen masks 10.

In the receptacle 2, the oxygen masks 10 are arranged in the usual manner such that they fall out of the receptacle 2 following a pressure drop in the cabin. When the users of the oxygen masks 10 pull these closer to themselves, an opening mechanism on the oxygen cylinder 4 is activated by pull means 14 which are attached on the oxygen masks 10, the so-called lanyards 14, so that oxygen may flow out of the oxygen cylinder 4 to the oxygen masks 10.

In the flow control device 12, the oxygen conduit 8 is part of a conduit system and divides into two or more parallel conduit lines, which are subsequently led together again into a single conduit, wherein an electrically activatable shut-off valve is arranged in each of the conduit lines. In this context, a solenoid valve 16 with an NO-function is arranged in one of the conduit lines, and in each case a solenoid valve 18 with an NC-function is arranged in the two remaining conduit lines. It is to be understood that one may also provide only two of such parallel conduit lines or more than three parallel conduit lines, e.g, depending on the required flow.

The activation of the solenoid valves 16 and 18 is effected by way of an electronic control device 20. For this, the solenoid valves 18 are connected to the control device 20 via signal connection 22 and 24, and the solenoid valve 16 to the control device 20 via a signal connection 26. The control device 20 controls the solenoid valves 16 and 18 on the basis of a cabin pressure, the oxygen pressure downstream of the pressure reducer 6, as well as the temperature of the oxygen.

A cabin pressure sensor 28 which is signal-connected to the control device 20 via a signal connection 30, is provided for determining the cabin pressure. The oxygen pressure is determined with an oxygen pressure sensor 32 which is arranged in the oxygen conduit 8 upstream of the solenoid valves 16 and 18 and which is signal-connected to the control device 20 by a signal connection 34. Moreover, a temperature sensor 36 is provided in the oxygen conduit 8, likewise upstream of the solenoid valves 16 and 18, and this temperature sensor 36 communicates with the control device 20 via a signal connection 38.

The cabin pressure sensor 28, the oxygen pressure sensor 32, the temperature sensor 36 and the solenoid valves 16 and 18 are arranged together with the control device 20 on a control panel 40. This also applies to an optical operating condition display 42, to which the control device 20 is connected via a signal lead 44. One may recognize whether the emergency oxygen supply device is in a correct condition or is not operationally ready, with the help of the operating condition display 42.

The manner of functioning of the represented emergency oxygen supply device is as follows:

If a pressure drop occurs in the passenger cabin of an aircraft, the oxygen masks 10 fall out of the receptacles 2. When the passengers pull the oxygen masks 10 in the direction of their face, the oxygen cylinder 4 is mechanically opened by way of the lanyard 14 which are connected to the oxygen masks 10. Oxygen now flows from the oxygen cylinder 4 via the pressure reducer 6 into the oxygen conduit 8. The cabin pressure and thus indirectly the flight altitude is detected by the cabin pressure sensor 28. Simultaneously, the oxygen pressure sensor 32 detects the pressure at the exit side of the pressure reducer 6, and the temperature sensor 36 detects the oxygen temperature. The electronic control device 20 determines the opening and closure times of the solenoid valves 16 and 18 on the basis of these values.

If the aircraft is located at a flight altitude above a dedicated flight altitude related to number of masks attached to the flow control device 12, the control device 20 causes the solenoid valve 16 to remain set in a constantly open manner, thus is not applied to voltage. Additionally, one of the two exchange magnets with solenoid valves 18 or both magnet valves 18 are applied to a voltage in intervals, so that additionally to the constant oxygen flow through the open solenoid valve 16, they lead oxygen to the oxygen masks 10 in a cycled manner. Oxygen intermediate storage means 46 which are formed on the oxygen masks 10 have the effect that an essentially continuous oxygen flow is available to the users of the oxygen masks 10.

If the aircraft descends to a flight altitude below the dedicated flight altitude, the solenoid valves 18 are no longer subjected to voltage, so that they remain closed and the oxygen supply of the oxygen masks 10 continues to be effected only via the open solenoid valve 16. With a further dropping fight altitude, the solenoid valve 16 is also set to close by way of subjecting it to voltage at intervals, until, from a second limit flight altitude of e.g, approx, 10,000 ft and below, where the cabin pressure is so high that a use of the oxygen masks 10 is no longer necessary, it is held closed in a constant manner by being subjected to voltage in an uninterrupted manner.

If with regard to the emergency oxygen supply device, a failure of the electrical energy supply takes place, then the solenoid valve 16 which is set to open per se when no voltage is applied, at least ensures a basic oxygen supply to the users of the oxygen masks 10.

While specific embodiments of the invention have been described in detail to illustrate the application of the principles of the invention, it will be understood that the invention may be embodied otherwise without departing from such principles.

What is claimed is:

1. An emergency oxygen supply device for an aircraft, the emergency oxygen supply device comprising:
- an oxygen pressure tank;
- an oxygen mask;
- a conduit from the oxygen pressure tank to the oxygen mask, the oxygen mask being conductively connected to the oxygen pressure tank via the conduit; and
- at least two electrically actuatable and activatable shut-off valves arranged parallel to one another in the conduit from the oxygen pressure tank to the at least one oxygen mask, the two electrically actuatable and activatable shut-off valves including at least one shut-off valve that has an NO-function and at least one shut-off valve that has an NC-function.

2. The emergency oxygen supply device according to claim 1, further comprising an electronic control device wherein the shut-off valves are activated by the electronic control device.

3. The emergency oxygen supply device according to claim 2, further comprising a cabin pressure sensor signal-connected to the control device for providing a cabin pressure signal to the control device.

4. The emergency oxygen supply device according to claim 2, further comprising an oxygen pressure sensor arranged in the supply conduit at the entry side of the shut-off valves and signal-connected to the control device for providing an oxygen pressure signal to the control device.

5. The emergency oxygen supply device according to claim 3, further comprising an oxygen pressure sensor arranged in the supply conduit at the entry side of the shut-off valves and signal-connected to the control device for providing an oxygen pressure signal to the control device.

6. The emergency oxygen supply device according to claim 2, further comprising a temperature sensor arranged in the supply conduit on the entry side of the shut-off valves and signal-connected to the control device for providing a temperature signal to the control device.

7. The emergency oxygen supply device according to claim 3, further comprising a temperature sensor arranged in the supply conduit on the entry side of the shut-off valves and connected to the control device, the temperature sensor providing a temperature signal to the control device.

8. The emergency oxygen supply device according to claim 3, wherein the cabin pressure sensor is arranged on a control panel of the control device.

9. The emergency oxygen supply device according to claim 4, wherein the oxygen pressure sensor is arranged on a control panel of the control device.

10. The emergency oxygen supply device according to claim 6, wherein the temperature sensor is arranged on a control panel of the control device.

11. The emergency oxygen supply device according to claim 1, wherein a compensation chamber is formed on the exit side of the shut-off valves.

12. An aircraft emergency oxygen supply device comprising:
- an oxygen pressure tank;
- an oxygen mask;
- a conduit system from the oxygen pressure tank to the oxygen mask, the conduit system including parallel conduit lines, the oxygen mask being conductively connected to the oxygen pressure tank via the conduit system;
- a first electrically actuatable and activatable shut-off valve arranged in one of the parallel conduit lines, the first electrically actuatable and activatable shut-off valve being normally open for allowing gas flow from the oxygen pressure tank to the at least one oxygen mask without a control voltage applied to the first electrically actuatable and activatable shut-off valve; and
- a second electrically actuatable and activatable shut-off valve arranged in another of the parallel conduit lines, the second electrically actuatable and activatable shut-off valve being normally closed for not allowing gas flow from the oxygen pressure tank to the at least one oxygen mask without a control voltage applied to the first electrically actuatable and activatable shut-off valve.

13. The emergency oxygen supply device according to claim 12, further comprising an electronic control device connected to each of the first electrically actuatable and activatable shut-off valve and the second electrically actuatable and activatable shut-off valve wherein the shut-off valves are activated for changing a flow state from normally open to closed or from normally closed to open by the electronic control device applying a control voltage thereto or changing a control voltage applied thereto.

14. The emergency oxygen supply device according to claim 13, further comprising a cabin pressure sensor signal-connected to the control device for providing a cabin pressure signal to the control device.

15. The emergency oxygen supply device according to claim 14, further comprising an oxygen pressure sensor arranged in the supply conduit at the entry side of the shut-off valves and signal-connected to the control device for providing an oxygen pressure signal to the control device.

16. The emergency oxygen supply device according to claim 15, further comprising a temperature sensor arranged in the supply conduit on the entry side of the shut-off valves and signal-connected to the control device for providing a temperature signal to the control device.

17. The emergency oxygen supply device according to claim 14, wherein the cabin pressure sensor is arranged on a control panel of the control device.

18. The emergency oxygen supply device according to claim 15, wherein the oxygen pressure sensor is arranged on a control panel of the control device.

19. The emergency oxygen supply device according to claim 16, wherein the temperature sensor is arranged on a control panel of the control device.

20. The emergency oxygen supply device according to claim 12, wherein a compensation chamber is formed on the exit side of the shut-off valves.

* * * * *